United States Patent [19]

Watson

[11] 4,373,534
[45] Feb. 15, 1983

[54] METHOD AND APPARATUS FOR CALIBRATING RESPIRATION MONITORING SYSTEM

[75] Inventor: Herman Watson, Miami, Fla.

[73] Assignee: Respitrace Corporation, Ardsley, N.Y.

[21] Appl. No.: 254,133

[22] Filed: Apr. 14, 1981

[51] Int. Cl.³ .............................................. A61B 5/10
[52] U.S. Cl. ................................... 128/725; 128/721
[58] Field of Search ................ 128/716, 719, 721–725, 128/694, 774–782; 73/728, 730–731, 735

[56] References Cited

U.S. PATENT DOCUMENTS

| | | | |
|---|---|---|---|
| 3,483,861 | 12/1969 | Tiep ..................................... | 128/721 |
| 3,782,368 | 1/1974 | Reibold ............................ | 128/721 X |
| 4,258,718 | 3/1981 | Goldman ......................... | 128/725 X |
| 4,267,845 | 5/1981 | Robertson, Jr. et al. ............ | 128/721 |
| 4,308,872 | 1/1982 | Watson et al. ................... | 128/721 X |

*Primary Examiner*—Lee S. Cohen
*Assistant Examiner*—Angela D. Sykes
*Attorney, Agent, or Firm*—Hubbell, Cohen, Stiefel & Gross

[57] ABSTRACT

Improved method for calibrating non-invasive system for measuring respiration volume of the type including apparatus for providing signals indicative of rib cage and abdominal contributions to respiration volume, device for multiplying the rib cage and abdominal signals by predetermined weighting factors reflecting the relative contributions of the rib cage and abdomen to respiration volume, and device for summing the weighted signals for providing a signal proportional to respiration volume. Improved method determines the weighting factors by measuring respiration volume by alternate measuring apparatus, simultaneously recording the unweighted rib cage and abdomen signals and the signal from the alternate measuring apparatus for a first plurality of breaths based on a first relative contribution between rib cage and abdomen and for a second plurality of breaths based on a second relative contribution between rib cage and abdomen, dividing the rib cage and abdomen signals by the signal from the alternate measuring apparatus for each breath for defining first and second coordinates for each breath, and determining the x and y intercepts of a line approximation extending through the plurality of points defined by the coordinates, the reciprocals of the intercepts substantially equaling the weighting factors.

2 Claims, 3 Drawing Figures

METHOD AND APPARATUS FOR CALIBRATING RESPIRATION MONITORING SYSTEM

TECHNICAL FIELD

This invention pertains to methods and apparatus for measuring respiration volume, and more particularly to such methods and apparatus which measure respiration volume by separately measuring and then summing the contributions from a plurality of torso portions, such as the rib cage and abdomen. Most particularly, this invention pertains to a calibration technique for weighting signals indicative of the contributions from the torso portions whereby the sum of the signals is proportional to respiration volume.

BACKGROUND ART

Application Ser. No. 102,408, now U.S. Pat. No. 4,308,872, filed Dec. 11, 1979, entitled Method and Apparatus For Monitoring Respiration, the contents of which are incorporated herein by reference in their entirety, discloses a method and apparatus for quantitatively measuring respiration volume. The method disclosed in the application comprises looping first and second extensible conductors about the rib cage and abdomen, separately and simultaneously measuring the inductances of the conductors during respiration, weighting the measured inductances to reflect the differing contributions of the rib cage and abdomen to respiration volume, and summing the weighted measured inductances to obtain actual respiration volume.

As noted, practice of the technique disclosed in the application requires weighting or calibrating the inductances measured by the abdomen and rib cage conductors. To effect calibration it is necessary to determine the weighting factors K and L to satisfy the following equation:

$$V = K \cdot RC + L \cdot AB \quad \text{(Equation A)}$$

where V is total respiration volume, RC is the rib cage contribution to respiration volume as measured at the rib cage conductor, and AB is the abdominal contribution as measured at the abdominal conductor. Application Ser. No. 102,408 discloses a specific technique for determining the values for the weighting factors K and L.

A spirometer is employed during the calibration procedure. With the patient in a first position, such as standing, a simultaneous set of readings are recorded from the outputs of the spirometer, the rib cage conductor, and the abdominal conductor. This is repeated with the patient in a second position, such as supine. At this point, there are two sets of values for V, RC, and AB which satisfy EQ. A. Thus, two equations having two unknowns, the constants K and L, may be written. From these, the weighting factors K and L may be determined by employing well known techniques for solving simultaneous equations. Thus:

$$K = \frac{AB_1 \cdot V_2 - AB_2 \cdot V_1}{RC_2 \cdot AB_1 - RC_1 \cdot AB_2} \quad \text{(Equation B)}$$

$$L = \frac{RC_1 \cdot V_2 - V_1 \cdot RC_2}{AB_2 \cdot RC_1 - AB_1 \cdot RC_2} \quad \text{(Equation C)}$$

The denominators of EQS. B and C may, depending upon the recorded values, approach or equal zero. Clearly, when this happens, the values obtained for K and L will be inaccurate, thereby skewing any measurement based on such weighting factors. Thus, each time the denominators of equations B and C approach or equal zero, a new set of readings must be taken, thereby increasing the time required for calibration. It is therefore an object of the present invention to provide an improved calibration method and apparatus which avoids this drawback.

DISCLOSURE OF THE INVENTION

Like the simultaneous equation technique disclosed in application U.S. Pat. No. 4,308,872, a spirometer or other device for measuring respiration volume is employed during the calibration procedure in accordance with the present invention. With the subject in a first position, readings from the spirometer, the rib cage conductor, and the abdominal conductor are simultaneously recorded for a plurality of breaths, preferably at least three in number. This is repeated with the subject in a second position. For each breath, the rib cage and abdominal readings are divided by the spirometer reading. That is, the values RC/V and AB/V are obtained for each breath, where V is the respiration volume as measured by the spirometer, RC is the rib cage reading from the uncalibrated rib cage conductor, and AB is the abdominal reading from the uncalibrated abdominal conductor.

The points (RC/V, AB/V) for each breath are then plotted on a graph whose axes are RC/V and AB/V. A line approximation is then drawn through these points. The line may be drawn by visual approximation, although preferably it is determined by the least squares technique. The line is then extended through the x and y axes. The reciprocals of the x and y intercepts define the weighting factors K and L, i.e. the reciprocal of the intercept of the RC/V axis defines the weighting factor K for the rib cage and the reciprocal of the intercept of the AB/V axis defines the weighting factor L for the abdomen.

Preferably, the data are not physically plotted on a graph and a line approximation drawn through the points for determining the intercepts. Rather, this is preferably carried out by a microprocessor or other data processor which performs the calculations internally and yields values for the weighting factors K and L.

The above as well as further features of the apparatus and method in accordance with the present invention will be more fully apparent from the following detailed description and annexed drawings of the presently preferred embodiment thereof.

BRIEF DESCRIPTION OF THE DRAWINGS

In the drawings:

FIG. 3 is a graph illustrating the calibration technique in accordance with the present invention.

BEST MODE FOR CARRYING OUT THE INVENTION

Figure 1:
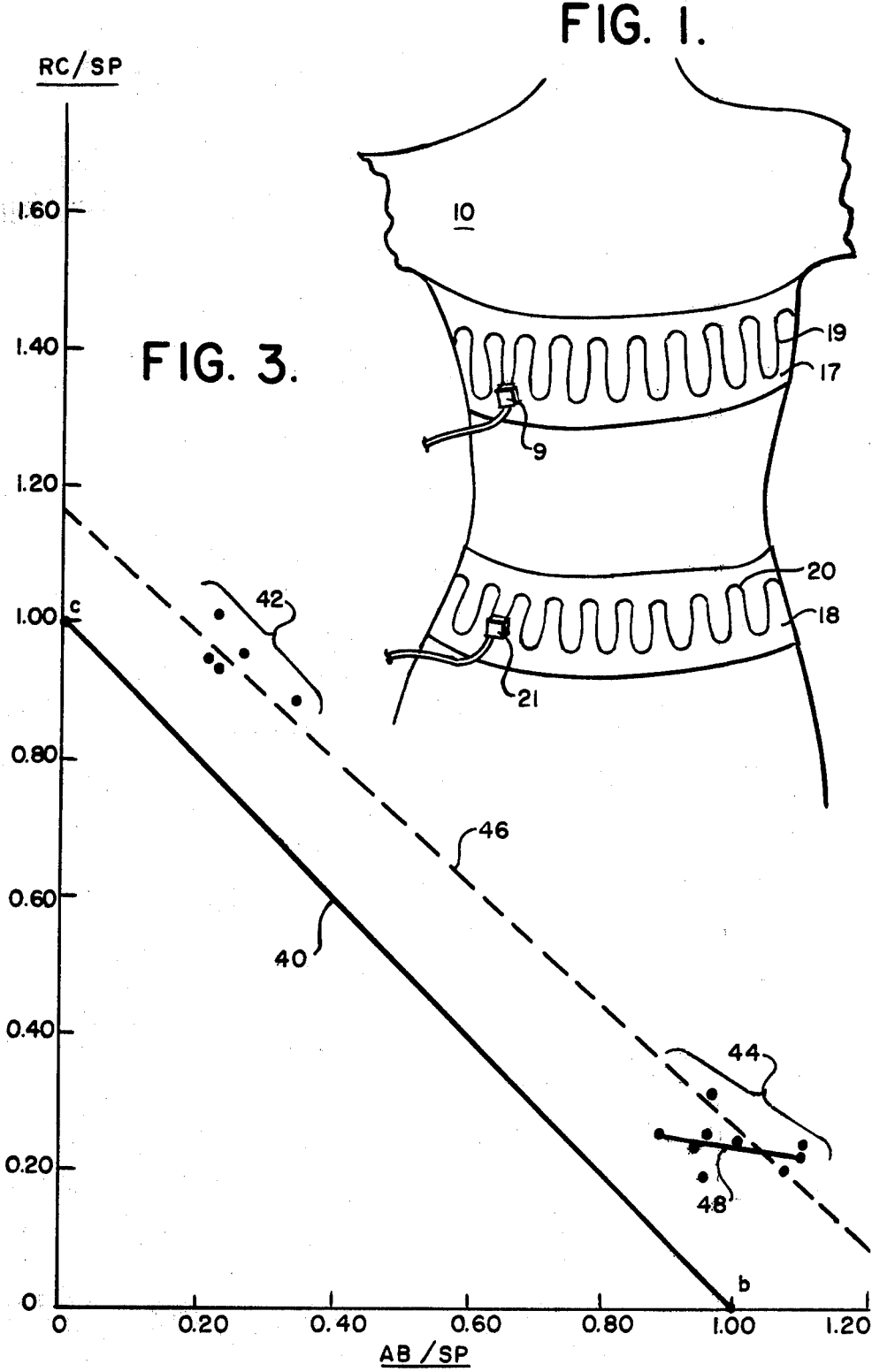
FIG. 1 is a digrammatic representation showing a portion of an apparatus for non-invasively monitoring respiration volume.
Figure 2:
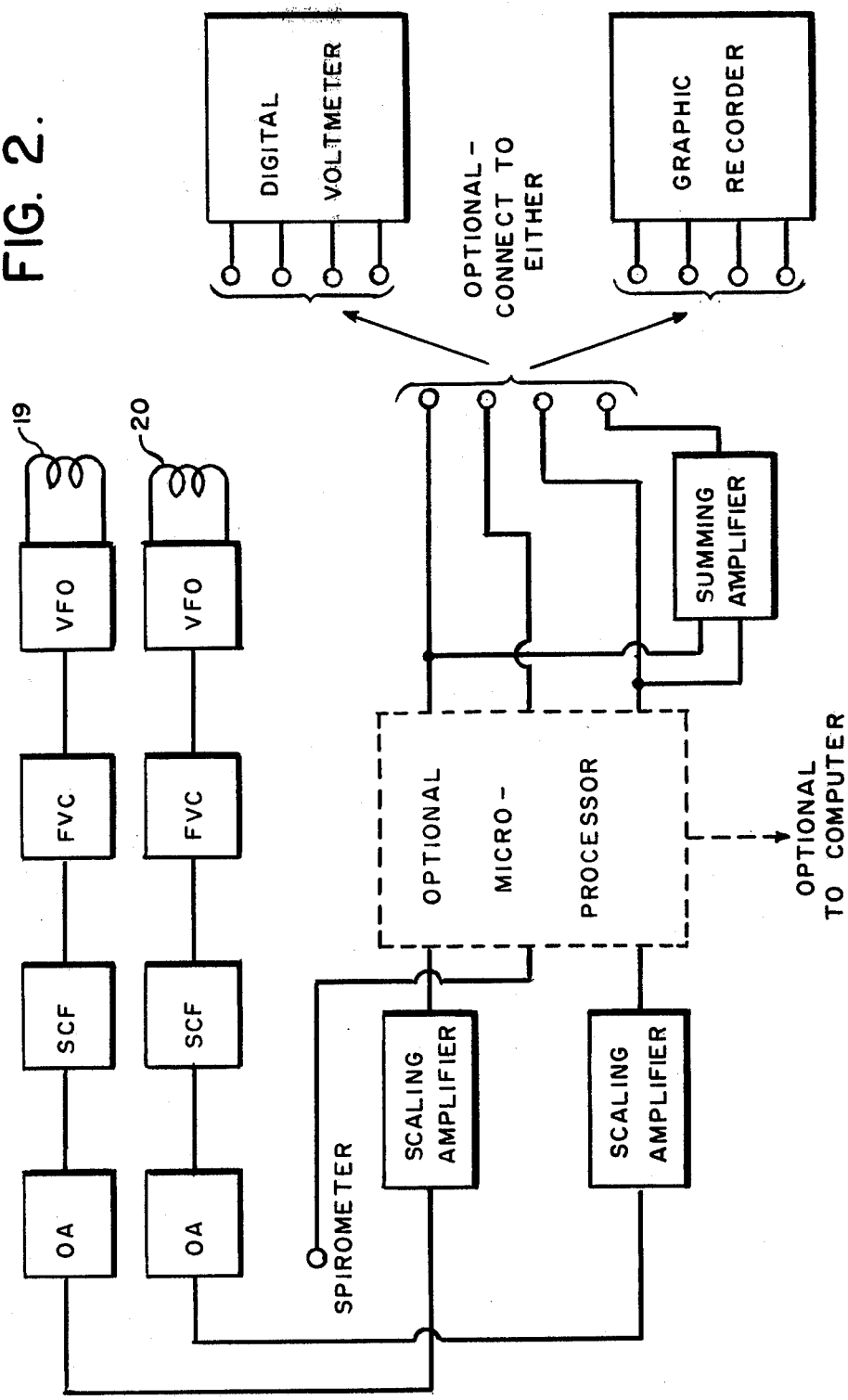
FIG. 2 is a block diagram showing circuitry useable in conjunction with the apparatus of FIG. 1.

Referring now to the drawings, and initially to FIGS. 1 and 2 thereof, apparatus for measuring respiration volume of the type disclosed in application U.S. Pat. No. 4,308,872 is shown. Two extensible conductive loops, 19, 20, are secured in any suitable fashion to elastic tubes, 17, 18, respectively, such that the conductors 19 and 20 extend respectively about the rib cage and abdomen of the subject 10. As the subject 10 breathes, elastic tubes 17, 18 and conductive loops 19, 20 expand and contract, resulting in changes in the cross sectional areas and hence in the inductances of the loops. As explained below, after the inductance of each loop is converted to an electrical signal, the signals are calibrated and then summed to provide an accurate measure of respiration volume.

A variable frequency oscillator (VFO) is connected to each of the two conductive loops, 19, 20. The resonant frequency of the oscillators is determined by an internal capacitor and the inductance of the conductive loop to which it is attached. This frequency may, for example, be centered about 300 KHz and will vary as the conductive loop it is connected to expands and contracts with respiration. To minimize artifacts, the oscillator electronics are preferably contained in modules 9 and 21 secured to the elastic tubes 17, 18, respectively.

The changes in frequency of the variable frequency oscillators with respiration are detected and converted to a DC signal by the frequency to voltage converters (FVC). The frequency to voltage converters may, for example, consist of DC restoration circuits and a simple diode detector for conversion of frequency.

The outputs of the frequency to voltage converters are connected to signal conditioning filters (SCF). The lower and higher cutoff frequencies of these filters may, for example, be set for about 0.05 and 10 Hz, respectively. The signal conditioning filters are followed by voltage amplifiers (OA) which boost the output signals to an amplitude of approximately 200 mV peak-to-peak for a one to two liter volume in adults.

As the subject 10 breathes to vary the enclosed areas and hence the inductances of conductive loops 19 and 20, the frequencies of the signals generated by the variable frequency oscillators also vary. These variations are detected by the frequency to voltage converters which will produce signals, preferably DC, dependent upon the detected variations. The signal conditioning filters clean up these signals, removing extraneous high and low frequency components. The outputs of the signal conditioning filters are then amplified by the operational amplifiers to provide a signal output of useful magnitudes.

Those skilled in the art may readily select available circuits to carry out the functions of the blocks VFO, FVC, SCF and OA in FIG. 2. By way of example, suitable circuitry is disclosed in application U.S. Pat. No. 4,308,872.

Referring again to FIG. 2, the outputs from the operational amplifiers are applied to scaling amplifiers, and the outputs of the scaling amplifiers are applied to a summing amplifier. When the scaling amplifiers are properly calibrated in the manner more fully explained below, the output of the summing amplifier will provide a signal proportional to actual respiration volume. This signal may be displayed, for example, on a digital voltmeter or a graphic recorder. Suitable circuitry for the scaling amplifiers and summing amplifier will also readily suggest themselves to those skilled in the art, and suitable circuits for these elements are also disclosed in application U.S. Pat. No. 4,308,872.

Referring now to FIGS. 1-3, the calibration technique in accordance with the present invention will now be described. During calibration, it is necessary to employ a standard respiration volume measurement device recognized as accurate, such as a spirometer. As shown in FIG. 2, the outputs from the spirometer and the scaling amplifiers for the rib cage and abdomen are each applied to a readout device, such as a digital voltmeter or graphic recorder. Preferably, although not necessarily, the scaling amplifiers for the chest and abdomen are each initially adjusted for unity gain. Also, a suitable DC offset is preferably applied to the output signal from the spirometer for compatibility with the graphic recorder, which may be a strip chart recorder.

For any given breath, it is known that $$\frac{RC}{SP} + \frac{AB}{SP} = 1 \qquad \text{(Equation D)}$$

where SP is total respiration volume as measured, e.g., by the spirometer, and RC and AB are the rib cage and abdomen contributions to total respiration volume, respectively, as measured, e.g., by the apparatus of FIGS. 1 and 2. Referring to the graph illustrated in FIG. 3, the abscissa of the graph is AB/SP and the ordinate is RC/SP. It is known from EQ. D that for a hypothetical breath wherein total respiration volume results solely from abdominal contribution, (AB/SP)=1.0. This point is indicated at b in FIG. 3. Likewise, for a hypothetical breath wherein respiration volume results solely from rib cage contribution, (RC/SP)=1.0. This point is indicated at c in FIG. 3. Since the two points b, c on the line defined by EQ. D are known, the line representing all points satisfying EQ. D may be drawn. This is the line 40 in FIG. 3. For any given breath, if point (AB/SP, RC/SP) is plotted, it will fall on the line 40.

Of course, the point (AB/SP, RC/SP) for a breath will only fall on the line 40 if the values for RC and AB accurately reflect the relative contributions of the rib cage and abdomen to total respiration volume. As noted above, in the system illustrated in FIGS. 1 and 2, this requires that the gain of the scaling amplifiers for the rib cage and abdomen signals be properly adjusted. This is accomplished in the manner described below.

For each of two positions of the subject 10, e.g. standing and supine, the outputs from the spirometer (SP) and from the chest (RC) and abdomen (AB) scaling amplifiers are recorded for a plurality of breaths, preferably at least three breaths for each position. This provides values for SP, RC, and AB for each breath.

Referring again to FIG. 3, the point (AB/SP, RC/SP) for each breath is then plotted. In FIG. 3, the points 42 correspond to measurements taken with the subject 10 standing, and the points 44 correspond to measurements taken with the subject supine. As shown in FIG. 3, five points 42 are plotted for the standing position, and nine points 44 for the supine position. However, and as indicated above, it is only necessary that a plurality of points, preferably at least three in number, are plotted for each position.

It is apparent from FIG. 3 that the points 42 and 44 do not fall in the vicinity of the line 40, which indicates that the scaling amplifiers for the rib cage and abdomen signals in FIG. 2 do not accurately reflect the relative contributions of rib cage and abdomen to total respiration volume. To find the proper scaling factors, an average value for each group of points 42, 44 is taken. This yields two "average" points 42, 44 through which a line 46 may be drawn. That is, the line 46 approximates a plot of all points (AB/SP, RC/SP) based on measurements taken with the apparatus of FIGS. 1 and 2 prior to calibration of the scaling amplifiers. If, as shown in FIG. 3, the line 46 is extended, the reciprocals of its ordinate and abscissa intercepts will provide the appropriate scaling factors for the rib cage and abdomen, respectively. That is, if the gains of the rib cage and abdomen scaling amplifiers are multiplied by the reciprocals of the y and x intercepts, respectively, the apparatus of FIGS. 1 and 2 will be properly calibrated for all breaths of the subject 10.

Referring to FIG. 3, the ordinate intercept is approximately 1.18, and the abscissa intercept is approximately 1.30. Therefore, the reciprocal of the ordinate intercept is $(1/1.18) = 0.85$ and the reciprocal of the abscissa intercept is $(1/1.30) = 0.77$. In the example given, the gains of the scaling amplifiers were initially set at 1.0. Consequently, the calibrated gain setting for the rib cage scaling amplifier is $(0.85) \times (1.0) = 0.85$, and the abdomen scaling amplifier is $(0.77) \times (1.0) = 0.77$. After calibration, the plot of points (AB/SP, RC/SP) based on measurements with the apparatus of FIGS. 1 and 2 will fall on the line 40. Actually, the plot of points AB/SP, RC/SP will predominately fall near the line 40, rather than directly on it, due to inaccuracies inherent in all non-invasive respiration volume measurement apparatus, including that illustrated in FIGS. 1 and 2. Nevertheless, when the apparatus of FIGS. 1 and 2 is calibrated using the technique described hereinabove, it has been found that in normal patients and those with mild airway obstructions substantially all breaths fall within ±2% of the actual respiration volume as measured with a spirometer.

In practice, once the apparatus of FIGS. 1 and 2 is calibrated in the manner described above, the spirometer may be discarded. Actual respiration volume may then be read at the output of the summing amplifier in FIG. 2. Of course, it will be necessary to recalibrate the apparatus for each different subject.

In the foregoing description of the calibration technique in accordance with the present invention, the line 46 is described as being drawn through two points representing the averages of the points 42 and 44. Alternatively, the least squares technique may be utilized to yield the minimum error line for the points 42, 44. The least squares technique is described, for example, at page 790 of the Handbook of Mathemathical Functions with Formulas, Graphs and Mathematical Tables, published by The National Bureau of Standards, 1965, Library of Congress Catalog Number 64-60036. As a still further alternative, the line 46 may be drawn by visual approximation. At present, for reasons of accuracy, the least squares technique is preferred.

As noted, a plurality of breath measurements are taken with the subject 10 in each of two positions, such as standing and supine. Referring to FIG. 3, this provides two spaced apart clusters of points 42, 44, which facilitate plotting of the line 46. For example, if the least squares technique is utilized to yield the minimum error line for the points 44 alone, it yields the line 48 in FIG. 3, which extends in quite a different direction from the line 46. Of course, positions other than standing and supine may be used and, if desired, more than two such positions may be used. Actually, any maneuver performed by the subject 10 which varies the relative contributions of rib cage and abdomen to respiration volume will suffice. Thus, it is not necessary that the subject actually change positions. He may, for example, rebreathe into a closed spirometer which, due to the build up of $CO_2$, gradually results in a shift of the relative contributions of rib cage and abdomen. The system and calibration technique may also be used on non-human subjects. To shift the relative contributions of the rib cage and abdomen as is required for calibration, a belt disposed about the rib cage or abdomen of the animal may be employed. For example, a belt tightened about the abdomen results in a first relative contribution, and removal of the belt results in a second relative contribution.

It will now be apparent that it is not necessary to actually plot the points 42, 44 on a graph such as that illustrated in FIG. 3 in order to obtain the intercepts of the line 46. The calculations may be carried out automatically by a microprocessor or other data processor as is diagrammatically illustrated in FIG. 2, and this is presently preferred. In such event, the breath data could be stored simultaneously in a computer and on the graphic recorder.

While I have herein shown and described the preferred embodiment of the present invention and have suggested certain modifications thereto, it will be apparent that further changes and modifications may be made without departing from the spirit and scope of the invention. Accordingly, the above description should be construed as illustrative and not in the limiting sense, the scope of the invention being defined by the following claims.

I claim:

1. In a non-invasive system for measuring respiration volume of the type including: means for providing a signal responsive to a rib cage dimension indicative of rib cage contribution to respiration volume; means for providing a signal responsive to an abdominal dimension indicative of abdominal contribution to respiration volume; means for multiplying said rib cage and abdominal signals by predetermined weighting factors reflecting the relative contributions of said rib cage and abdomen to respiration volume; and means for summing said weighted signals for providing a signal proportional to respiration volume; the improvement comprising means for determining said weighting factors comprising:

alternate means for measuring respiration volume and providing a signal indicative thereof;

means for simultaneously recording said unweighted rib cage and abdominal signals and said signal from said alternate measuring means for a first plurality of breaths based on a first relative contribution between said rib cage and abdomen and for a second plurality of breaths based on a second relative contribution between said rib cage and abdomen;

processing means for (1) dividing said rib cage signal by said signal from said alternate measuring means for each breath for definig a first coordinate for each breath, (2) dividing said abdominal signal by said signal from said alternate measuring means for each breath for defining a second coordinate for each breath, and (3) determining the x and y intercepts of a line approximation extending through the plurality of points defined by said first and second coordinates, the reciprocals of said intercepts substantially equaling said weighting factors.

2. In a method for non-invasively measuring respiration volume of the type including: providing a signal responsive to a rib cage dimension indicative of rib cage contribution to respiration volume; providing a signal responsive to an abdominal dimension indicative of abdominal contribution to respiration volume; multiplying said rib cage and abdominal signals by predetermined weighting factors reflecting the relative contributions of said rib cage and abdomen to respiration volume; and summing said weighted signals for providing a signal proportional to respiration volume; the improvement comprising determining said weighting factors by:

measuring respiration volume by alternate measuring means and providing a signal indicative thereof;

simultaneously recording said unweighted rib cage and abdominal signals and said signal from said alternate measuring means for a first plurality of breaths based on a first relative contribution between said rib cage and abdomen and for a second plurality of breaths based on a second relative contribution between said rib cage and abdomen;

dividing said rib cage signal by said signal from said alternate measuring means for each breath for defining a first coordinate for each breath, dividing said abdominal signal by said signal from said alternate measuring means for each breath for defining a second coordinate for each breath, and determining the x and y intercepts of a line approximation extending through the plurality of points defined by said first and second coordinates, the reciprocals of said intercepts substantially equaling said weighting factors.

* * * * *